(12) United States Patent
Ryu et al.

(10) Patent No.: US 8,716,192 B2
(45) Date of Patent: May 6, 2014

(54) MICRO RNAS FOR IDENTIFICATION OF EXPOSURE TO LOWER ALIPHATIC SATURATED ALDEHYDES AND THE METHOD OF IDENTIFICATION USING THEREOF

(71) Applicant: Korea Institute of Science and Technology, Seoul (KR)

(72) Inventors: Jae Chun Ryu, Seoul (KR); Mee Song, Seoul (KR); Ji-seong Yoon, Seoul (KR); Wooin Ryu, Seoul (KR); Hyo Sun Lee, Seoul (KR); Chan Young Shin, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/689,216

(22) Filed: Nov. 29, 2012

(65) Prior Publication Data

US 2013/0324429 A1 Dec. 5, 2013

(30) Foreign Application Priority Data

May 30, 2012 (KR) ........................ 10-2012-0057452

(51) Int. Cl.
*C12Q 1/68* (2006.01)

(52) U.S. Cl.
USPC ............................................. 506/9; 435/6.12

(58) Field of Classification Search
CPC ........ C12Q 1/68; C12Q 1/686; C12Q 1/6837; C12Q 1/6886
USPC ............................................. 506/9; 435/6.16
See application file for complete search history.

(56) References Cited

FOREIGN PATENT DOCUMENTS

WO     WO 2011080318 A1 *  7/2011

OTHER PUBLICATIONS

Pal et al., The Pollution Status of Atomspheric Carbonyls in a Highly Industrialized Area, J. Hazardous Materials, 2008, 153, 1122-1135.*
Rager, J., A Systems Biology Approach to Investigate Human Lung Cell Response to Air Pollutants, 2010, Thesis, University of North Carolina at Chapel Hill, 1-103.*
H.F. Hubbard, et al., Application of Novel Method to Measure Endogenous VOCs . . . , Journal of Chromatography B, 877, pp. 3652-3658, 2009.
Diana Poli, et al., Dtermination of Aldehydes in Exhaled . . . , Journal of Chromatography B, 878, pp. 2643-2651, 2010.
Patricia Fuchs, et al., Breath Gas Aldehydes as Biomarkers of Lung Cancer., Int. J. Cancer, 126, pp. 2663-2670, 2010.

* cited by examiner

*Primary Examiner* — Maria Leavitt
*Assistant Examiner* — Amy M Bunker
(74) *Attorney, Agent, or Firm* — Lucas & Mercanti, LLP (57) ABSTRACT

The present invention relates to a biomarker for the identification of exposure to lower aliphatic saturated aldehydes by using micro RNA and a method for the identification of exposure to lower aliphatic saturated aldehydes using the same. In this invention, the micro RNA at least 1.5 fold up-regulated by exposure to lower aliphatic saturated aldehydes and the micro RNA up to 0.66 fold down-regulated by the same were selected. These two micro RNAs can be effectively used as the biomarker for the monitoring of lower aliphatic saturated aldehydes and for the risk assessment thereby and at the same time as a tool to investigate the mechanism of toxicity caused by such lower aliphatic saturated aldehydes.

9 Claims, 3 Drawing Sheets

```
SEQUENCE LISTING

<160> NUMBER OF SEQ ID NOS: 2

<210> SEQ ID NO 1
<211> LENGTH: 22
<212> TYPE: RNA
<213> ORGANISM: Artificial Sequence
<220> FEATURE:
<223> OTHER INFORMATION: hsa-miR-590-5p MIMAT0003258

<400> SEQUENCE: 1
gagcuuauuc auaaaagugc ag                                          22

<210> SEQ ID NO 2
<211> LENGTH: 22
<212> TYPE: RNA
<213> ORGANISM: Artificial Sequence
<220> FEATURE:
<223> OTHER INFORMATION: hsa-miR-28-5p MIMAT0000085

<400> SEQUENCE: 2
aaggagcuca cagucuauug ag                                          22
```

MICRO RNAS FOR IDENTIFICATION OF EXPOSURE TO LOWER ALIPHATIC SATURATED ALDEHYDES AND THE METHOD OF IDENTIFICATION USING THEREOF

CROSS-REFERENCES TO RELATED APPLICATION

This patent application claims the benefit of priority under 35 U.S.C. §119 from Korean Patent Application Nos. 10-2012-0057452 filed on May 30, 2012 the contents of which are incorporated herein by reference.

BACKGROUND OF THE INVENTION

1. Field of the Invention

The present invention relates to a microRNA for the identification of exposure to lower aliphatic saturated aldehydes and a method for the identification thereof using the same, more precisely a microRNA whose expression is changed specifically by the treatment of aldehydes at the concentration demonstrating 80% cell survival rate and a method for the identification of exposure to such aldehydes using the same.

2. Description of the Related Art

Micro RNA (miR, miRNA) has been recently on the rise as the important regulative RNA affecting a variety of biological processes. These small non-coding RNAs (typically 18-24 nucleotides long) are able to accelerate RNA degradation, inhibit mRNA translation, and regulate protein expression pattern by affecting gene transcription. Micro RNA plays a key role in a variety of biological processes such as development and differentiation, cell proliferation control, stress response, and metabolism, etc. Approximately 1000 human micro RNAs are known so far.

Micro RNA is transcribed by RNA polymerase II (pol II) or RNA polymerase III (pol III; Qi, P. et al. *Cell. Mol. Immunol.* 3, 411-419, 2006), and can be induced from each microRNA gene, intron of a gene encoding protein, or poly-cistron transcripts encoding mainly mRNAs closely related to each other. Transcription of miRNA by RNA pol II or pol III produces the first transcript, which is so called primary miRNA transcript (pri-miRNAs) in the length of thousands of nucleotides. In nucleus, pri-miRNAs are processed by RNAse, Drosha, to produce 70-100 nucleotide long hairpin shaped pre-miRNAs. After being transferred in cytoplasm, hairpin pre-miRNA is additionally processed by dicer to produce double-stranded miRNA. Mature miRNA strand is mixed in RNA-induced silencing complex (RISC) for the binding with target mRNAs based on base pair complementarity. If miRNA base pairs are consistant with target mRNAs, which is very rare though, it accelerates the degradation of mRNA. More generally, miRNAs form heteroduplex with target mRNAs, which affects mRNA translation.

Micro RNA mechanism greatly affects cancer development, cellular aging, and organ growth, etc. Therefore, the micro RNA related studies not only play a key role in explaining casual relations of vital phenomena such as cancer development and aging, etc, but also can be applied to further studies in relation to development and differentiation and for the development of cell therapy products using stem cells, indicating those studies may be the core of future bio-studies in Korea. Therefore, the development of micro RNA marker is important since it can help early diagnosis and prediction of diseases including cancer.

Besides, micro RNA marker is expected to be effectively used for the prediction of exposure to a specific environmental hazardous substance. Studies have been focused so far on the investigation of gene (mRNA) changes caused by such environmental hazardous substances and the relation with disease thereby. However, according to the recent increase of interest in micro RNA, the expression changes of micro RNA caused by exposure to harmful substances such as benzene, arsenic or RDX, etc, have been investigated in recent studies and thereby the micro RNA whose expression is specifically changed by the said substances and target genes thereof have been proposed as markers for the harmful substances (Baccarelli, A. & Bollati, V. *Curr. Opin. Prediatr.* 21, 243-251, 2009). Micro RNA is believed to be an effective marker not only for the prediction of exposure but also for the prediction of toxic mechanism caused by environmental hazardous substances and an effective regulator controlling target gene expression as well. Although micro RNA marker is a key player in the prediction of exposure to environmental hazardous substance and toxic mechanism thereof, the studies on micro RNA have been limited to the development of a marker for diagnosis of disease and the studies on the expression changes of micro RNA caused by exposure to harmful substances such as aldehydes which are so easy to be exposed on various environments are still insufficient. Epigenetic changes are not as big as the diversity of genetic changes including gene expression. Therefore, compared with gene expression profiling requiring multiple markers, disease or harmful substance exposure can be early diagnosed with simple epigenetic marker such as micro RNA or DNA methylation. The said diagnosis can be performed by non-invasive methods. Each micro RNA regulates different target genes. Higher eukaryote has thousands of micro RNAs, suggesting that potential circuits that can be regulated by micro RNA seem to be very huge.

Among many aldehydes, lower aliphatic saturated aldehydes have $C_0$~$C_9$ carbon chain. Each of them is gas or liquid having pungent odor and dissolved in water. Among them, aldehydes having $C_6$~$C_9$ carbon chain are mainly used as flavorings or food additives, or used in perfume industry. The indoor or outdoor concentrations of lower aliphatic saturated aldehydes have not been fully investigated since 8 kinds of aldehydes except formaldehyde and acetaldehyde have not been classified as hazardous materials or targets for regulation, yet. According to the previous reports rarely made, the exposure level of lower aliphatic saturated aldehydes has not been regular. For example, the exposure level in indoor environment was varied from conditions of the building and surrounding environment. Only Korea and Japan have the regulation on lower aliphatic saturated aldehydes, which is exemplified by propionaldehyde, butylaldehyde, and pentylaldehyde (only three of them).

Once exposed to a low concentration of lower aliphatic saturated aldehyde, such symptoms as ocular irritation and respiratory irritation are developed. When a high concentration of the lower aliphatic saturated aldehyde is inhaled, respiratory system is irritated, resulting in such symptoms as burning feeling, nausea, dizziness, cough, phlegm, laryngitis, headache, respiratory rate increase, and dyspnea. When the said aldehyde is inhaled for a long term, convulsion, seizure, bronchitis, pneumonia, and laryngeal edema can be developed (www.toxnet.nlm.nih.gov). The in vivo function of lower aliphatic saturated aldehyde is to induce carbonylation of nucleic acid and protein to cause mutation or to induce oxidation to cause cytotoxicity (*Crit Rev Toxicol* 35(7):609-662, 2005).

The volatile organic compounds flowing through bloodstream affect the lung by diffusion of lung sac membrane. Hexane, methylpentan, isopropene, and benzene have been used as markers for the respiratory diseases (*J Vet Sci* 5(1): 11-18, 2004). Recently, a simple diagnostic method for lung cancer has been developed based on the results of exhaled breath analysis on volatile organic compounds. Among the volatile organic compounds, aldehydes are the most representative materials commonly found in lung cancer patients (*J Chromatogr B Analyt Technol Biomed Life Sci.* 878(27): 2643-2651, 2010). Therefore, the lower aliphatic saturated aldehyde specific biomarker can be effectively used for the screening of exposure to lower aliphatic saturated aldehyde in the environment along with the screening of pulmonary disease. Once exposed to aldehydes, bronchus related symptoms are mainly developed, which are cough, phlegm, laryngitis, nausea, asthma, and dizziness, etc. If it gets worse, such diseases as pneumonia, laryngeal edema, bronchitis, and seizure can be developed (www.toxnet.nlm.nih.gov).

Despite the hazard in human, risk assessment data of lower aliphatic saturated aldehyde are not enough. Recently, microarray chip is widely used for the diagnosis of diseases. However, the methods for the screening of exposure to environmental hazardous substance are limited to a few classical methods such as GC-MS (Gas Chromatography-Mass Spectrometer) or HPLC (High Performance Liquid Chromatography). GC-MS or HPLC enables quantitative analysis but proper conditions have to be set up first and expensive equipments are required for the analysis. Therefore, faster and simpler screening method, such as real-time RT-PCR using microarray chip or primer is more recommended to evaluate risk quickly. Thus, it is important to establish molecular index for the screening of toxicity, especially micro RNA expression pattern involved in various diseases including cancer via faster and simpler methods such as real-time RT-PCR (real-time reverse transcript polymerase chain reaction) using primers or microarray chip for the fast risk assessment, and so is to control and manage the exposure to lower aliphatic saturated aldehydes.

Ever since micro RNA was first identified in 1997, many kinds of micro RNAs have been rapidly identified from mammals and microorganisms, which were reported to Sanger miRBASE database (www.mirbase.org/index.shtml) Based on the micro RNA data established so far, genome-wide expression studies have been actively undergoing to disclose gene functions. Microarray assay is generally used to analyze the expressions of thousands of genes at a time (Schena, M, et al. *Proc. Natl. Acad. Sci. USA* 93, 10614-10619, 1996).

Microarray indicates the glass board on which many sets of cDNA (complementary DNA) or 20-25 base pair long oligonucleotides are integrated. cDNA microarray is now produced by ink jetting or by fixing cDNA mechanically on the chip in laboratories of schools or companies including Agilent and Genomic Solutions, etc. (Sellheyer K. et. al. *J. Am. Acad. Dermatol.* 51, 681-692, 2004). Oligonucleotide microarray is produced by direct synthesis on the chip using photolithography by Affymetrix Co., or via fixation of synthesized oligonucleotides by Agilent Co. (Sellheyer, K. et. al. *J. Am. Acad. Dermatol.* 51, 681-692, 2004).

To analyze gene expression, micro RNA is first obtained from samples such as tissues, etc., followed by hybridization with oligonucleotides on microarray. The obtained micro RNA is labeled with fluorescein or isotope.

The methods to analyze gene expression using microarray are largely divided into two ways; one is two-dye method and the other is one-dye method. When complementary binding is measured, the control and the experimental samples are labeled with different fluorescent materials (ex, Cye3 and Cye5), which proceed to the reaction with microarray. This is called two-dye microarray. If the control and the experimental samples are labeled with the same fluorescent material and then reacted with two different microarrays, it is called one-dye microarray (Vivian, G. et al. *Nature* 21, 15-19, 1999).

The cooperation with toxicogenomics, the most recent technology using DNA microarray, enables high throughput quantitative analysis and expression pattern analysis of micro RNAs expressed in a specific tissue or cell line triggered by every chemical including not only drugs and new drug candidates but also representative environmental contaminants. Thus, specific genes that are involved in side effects of drugs and adverse actions of environmental contaminants can be identified by analyzing specific micro RNA expression in specific cells. Accordingly, adverse actions of environmental contaminants and molecular mechanisms related to functions and side effects of drugs can be understood and further screening and identification of such material that causes toxicity and side effects can be achieved.

The present inventors observed and analyzed micro RNA expression profiles in A549, the human lung cancer cell derived cell line, treated with lower aliphatic saturated aldehydes at the concentration of $IC_{20}$ (the concentration showing 20% survival rate) by using oligomicroarray on which 1347 human micro RNAs were integrated. As a result, the micro RNA showing changes of expression specifically by lower aliphatic saturated aldehyde was identified. Accordingly, the present inventors completed this invention by establishing the method for the identification of exposure to lower aliphatic saturated aldehyde by using the micro RNA.

SUMMARY OF THE INVENTION

It is an object of the present invention to provide a micro RNA for the identification of exposure to lower aliphatic saturated aldehydes having toxicity to cause diverse diseases in human.

It is another object of the present invention to provide a method for the identification of exposure to lower aliphatic saturated aldehydes by using the micro RNA of the present invention.

To achieve the above objects, the present invention provides a microarray chip for the identification of exposure to lower aliphatic saturated aldehydes, on which one or more micro RNAs or their complementary strand molecules selected from the following group are integrated:

micro RNA accession number (miRbase) MIMAT0003258 (hsa-miR-590-5p, *Homo sapiens* miR-590-5p; SEQ. ID. NO: 1); and micro RNA accession number (miRbase) MIMAT0000085 (hsa-miR-28-5p, *Homo sapiens* miR-28-5p; SEQ. ID. NO: 2).

The present invention also provides a kit for the identification of exposure to lower aliphatic saturated aldehydes comprising the said microarray chip.

The present invention further provides a kit for the identification of exposure to lower aliphatic saturated aldehydes comprising the primer set that is complementary to one or more micro RNAs selected from the following group and is able to amplify the said micro RNA:

micro RNA accession number (miRbase) MIMAT0003258 (hsa-miR-590-5p, *Homo sapiens* miR-590-5p; SEQ. ID. NO: 1); and micro RNA accession number (miRbase) MIMAT0000085 (hsa-miR-28-5p, *Homo sapiens* miR-28-5p; SEQ. ID. NO: 2).

The present invention also provides a method for the identification of exposure to lower aliphatic saturated aldehydes, comprising the following steps:

1) measuring an expression level of micro RNA accession number (miRbase) MIMAT0003258 (hsa-miR-590-5p, *Homo sapiens* miR-590-5p; SEQ. ID. NO: 1), and micro RNA accession number (miRbase) MIMAT0000085 (hsa-miR-28-5p, *Homo sapiens* miR-28-5p; SEQ. ID. NO: 2), on somatic cells separated from both an experimental group and a normal control group; and 2) determining the experimental group to be exposed to lower aliphatic saturated aldehydes, if the expression of the micro RNA accession number (miRbase) MIMAT0003258 (hsa-miR-590-5p, *Homo sapiens* miR-590-5p; SEQ. ID. NO: 1), and the micro RNA accession number (miRbase) MIMAT0000085 (hsa-miR-28-5p, *Homo sapiens* miR-28-5p; SEQ. ID. NO: 2) on the somatic cells from the experimental group is up-regulated or down-regulated compared to the expression of the normal control group.

The present invention also provides a method for the identification of exposure to lower aliphatic saturated aldehydes comprising the following steps:

1) extracting RNA from somatic cells obtained from both the experimental group and the normal control group;

2) labeling the RNA obtained from both the experimental group and the control group of step 1) with different fluorescent materials;

3) hybridizing the RNA labeled with fluorescent materials of step 2) with the microarray chip of the present invention;

4) analyzing the microarray chip reacted in step 3); and 5) confirming the expression of the micro RNA integrated on the microarray chip of the present invention based on the analyzed data of step 4).

In addition, the present invention provides a method for the identification of exposure to lower aliphatic saturated aldehydes comprising the following steps:

1) extracting RNA from somatic cells obtained from both the experimental group and the normal control group;

2) synthesizing cDNA from the RNA obtained from both the experimental group and the control group of step 1);

3) performing real-time RT-PCR (real-time reverse transcript polymerase chain reaction) with the cDNA synthesized from the RNA obtained from both the experimental group and the control group of step 2) using the primer set which is able to amplify the micro RNA integrated on the microarray chip; and 4) confirming the expression of the amplified product of step 3) by comparing the expression of the experimental group with that of the control group.

Advantageous Effect

The present inventors selected 7 kinds of lower aliphatic saturated aldehydes as follows: propionaldehyde, butylaldehyde, valeraldehyde, hexanal, heptanal, octanal, and nonanal. The present inventors selected one micro RNA demonstrating at least 1.5 fold up-regulation by at least three kinds of the said aldehydes and the other micro RNA demonstrating up to 0.66 fold down-regulation by them. The selected two kinds of micro RNAs can be effectively used as the biomarker to be used for the monitoring and evaluation of risk of lower aliphatic saturated aldehydes and to be used as a tool to disclose toxic mechanism caused by the said lower aliphatic saturated aldehydes.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Hereinafter, the present invention is described in detail.

The present invention provides a biomarker for the identification of exposure to lower aliphatic saturated aldehydes whose expression is specifically changed by the exposure to lower aliphatic saturated aldehydes.

The said biomarker is composed of one micro RNA that is up-regulated by lower aliphatic saturated aldehyde specific exposure and the other micro RNA that is down-regulated by the same.

The said biomarker is preferably selected from the following group, but not always limited thereto:

micro RNA accession number (miRbase) MIMAT0003258 (hsa-miR-590-5p, *Homo sapiens* miR-590-5p; SEQ. ID. NO: 1); and micro RNA accession number (miRbase) MIMAT0000085 (hsa-miR-28-5p, *Homo sapiens* miR-28-5p; SEQ. ID. NO: 2).

To establish the biomarker for the identification of micro RNA expression by lower aliphatic saturated aldehydes, the present inventors investigated cytotoxicity by treating human lung cancer cell line A549 with lower aliphatic saturated aldehydes. As a result, the lower aliphatic saturated aldehydes were confirmed to have cytotoxicity in the human lung cancer cell line (see FIG. 1). Based on the above experiment, the concentration ($IC_{20}$: the concentration showing 20% survival rate) of lower aliphatic saturated aldehydes was determined. Then the lower aliphatic saturated aldehydes were treated to human lung cancer cell line. Total RNA containing micro RNA was extracted from the treated cell line, followed by labeling with Cy3. The fluorescein-labeled micro RNA was hybridized with Agilent Human miRNA array v16.0 (Agilent, USA), followed by scanning fluorescence image to analyze gene expression pattern. When the signal intensity rate of the experimental group to the control group was higher than 1.5, the micro RNA was regarded as the one whose expression is increased. When the ratio is lower than 0.66, the micro RNA was regarded as the one whose expression is decreased. As a result, in the sample treated with propionaldehyde at the concentration of $IC_{20}$, the up-regulated micro RNA took 0.97% (13 out of 1347 micro RNAs), and the down-regulated micro RNA took 0.15% (2 out of 1347 micro RNAs). In the sample treated with butylaldehyde, the up-regulated micro RNA took 1.04% (14 out of 1347 micro RNAs), and the down-regulated micro RNA took 0.82% (11 out of 1347 micro RNAs). In the sample treated with valeraldehyde, the over-expressed micro RNAs took 0.59% (8 out of 1347 micro RNAs) and the down-regulated micro RNAs took 0.15% (5 out of 1347 micro RNAs). In the sample treated with hexanal, the up-regulated micro RMA took 0.37% (5 out of 1347 micro RNAs), and the down-regulated micro RNA took 0.07% (1 out of 1347 micro RNAs). In the sample treated with heptanal, the up-regulated micro RNA took 0.00% (0 out of 1347 micro RNAs), and the down-regulated micro RNA took 0.30% (4 out of 1347 micro RNAs). In the sample treated with octanal, the up-regulated micro RNA took 0.07% (one out of 1347 micro RNAs), and the down-regulated micro RNA took 1.04% (14 out of 1347 micro RNAs). In the sample treated with nonanal, the up-regulated micro RNA took 0.45% (6 out of 1347 micro RNAs) and the down-regulated micro RNA took 0.00% (0 out of 1347 micro RNAs) (see FIG. 2). At that time, the micro RNA demonstrating at least 1.5 fold up-regulation by more than 3 kinds of lower aliphatic saturated aldehydes was only one kind, and the micro RNA demonstrating less than 0.66 fold down-regulation by the same was also only one kind (see Table 1).

The present inventors selected the micro RNA (only one) that showed over-expression among many micro RNAs and the micro RNA (only one) that showed lower-expression and then performed real-time RT-PCR (real-time reverse transcript polymerase chain reaction) to investigate the expression patterns. As a result, the expression patterns of the over-expressed micro RNA and the lower-expressed microRNA were similar to those obtained from the earlier experiment using oligomicroarray chip (see FIG. 3).

Accession numbers of the micro RNAs are as follows:

micro RNA accession number (miRbase) MIMAT0003258 (hsa-miR-590-5p, *Homo sapiens* miR-590-5p; SEQ. ID. NO: 1); and micro RNA accession number (miRbase) MIMAT0000085 (hsa-miR-28-5p, *Homo sapiens* miR-28-5p; SEQ. ID. NO: 2).

The present invention also provides a micro RNA microarray chip for the identification of exposure to lower aliphatic saturated aldehydes on which oligonucleotides containing a whole or a part of the micro RNA sequence of the said biomarker or complementary strand molecules thereof are integrated.

The said oligonucleotides or complementary strand molecules thereof contain 15-20 nucleic acids of the said biomarker micro RNA.

The DNA microarray chip for the identification of exposure to lower aliphatic saturated aldehydes of the present invention can be prepared by the method well known to those in the art. Particularly, the method for the preparation of the said microarray chip is as follows. To fix the screened biomarker on the board of chip using as a probe micro RNA molecule, ink-jetting method is preferably used, but not always limited thereto. In a preferred embodiment of the present invention, SurePrint inkjet micro dropping microarray was used. The microarray chip board is preferably coated with one of active groups selected from the group consisting of epoxy, amino-silane, poly-L-lysine, and aldehyde, but not always limited thereto. The board is also selected from the group consisting of slide glass, plastic, metal, silicon, nylon membrane, and nitrocellulose membrane, but not always limited thereto. In a preferred embodiment of the present invention, epoxy coated slide glass was used as the board.

The present invention also provides a method for the identification of exposure to lower aliphatic saturated aldehydes by using the said biomarker.

Particularly, the method is composed of the following steps:

1) measuring an expression level of micro RNA accession number (miRbase) MIMAT0003258 (hsa-miR-590-5p, *Homo sapiens* miR-590-5p; SEQ. ID. NO: 1), and micro RNA accession number (miRbase) MIMAT0000085 (hsa-miR-28-5p, *Homo sapiens* miR-28-5p; SEQ. ID. NO: 2), on somatic cells separated from both an experimental group and a normal control group; and 2) determining the experimental group to be exposed to lower aliphatic saturated aldehydes, if the expression of the micro RNA accession number (miRbase) MIMAT0003258 (hsa-miR-590-5p, *Homo sapiens* miR-590-5p; SEQ. ID. NO: 1), and the micro RNA accession number (miRbase) MIMAT0000085 (hsa-miR-28-5p, *Homo sapiens* miR-28-5p; SEQ. ID. NO: 2) on the somatic cells from the experimental group is up-regulated or down-regulated compared to the expression of the normal control group.

In the above method, the somatic cell of step 1) is preferably human lung cell or human lung cancer cell, but not always limited thereto, and in fact any cell derived from tissue can be used.

In the above method, the human lung cancer cell is preferably A549, but not always limited thereto.

In the above method, the lower aliphatic saturated aldehydes are propionaldehyde, butylaldehyde, valeraldehyde, hexanal, heptanal, octanal, and nonanal.

In the above method, the expression level of the micro RNA accession number (miRbase) MIMAT0003258 (hsa-miR-590-5p, *Homo sapiens* miR-590-5p; SEQ. ID. NO: 1) is up-regulated compared to the normal control group on propionaldehyde, valeraldehyde, and hexanal, and down-regulated compared to the normal control group on butylaldehyde, heptanal, octanal, and nonanal.

In the above method, the expression level of the micro RNA accession number (miRbase) MIMAT0000085 (hsa-miR-28-5p, *Homo sapiens* miR-28-5p; SEQ. ID. NO: 2) is up-regulated compared to the normal control group on propionaldehyde, valeraldehyde, hexanal, and nonanal, and down-regulated compared to the normal control group on heptanal, and octanal.

The present invention also provides a method for the identification of exposure to lower aliphatic saturated aldehydes by using the said biomarker.

Particularly, the method is composed of the following steps:

1) extracting RNA from somatic cells obtained from both the experimental group and the normal control group;

2) labeling the RNA obtained from both the experimental group and the control group of step 1) with different fluorescent materials;

3) hybridizing the RNA labeled with fluorescent materials of step 2) with the microarray chip of the present invention;

4) analyzing the microarray chip reacted in step 3); and 5) confirming the expression of the micro RNA integrated on the microarray chip of the present invention based on the analyzed data of step 4).

In the above method, the somatic cell of step 1) is preferably human lung cell or human lung cancer cell, but not always limited thereto, and in fact any cell derived from tissue can be used.

In the above method, the human lung cancer cell is preferably A549, but not always limited thereto.

In the above method, the fluorescent material of step 2) is preferably selected from the group consisting of Cy3, Cy5, poly L-lysine-fluorescein isothiocyanate (FITC), rhodamine-B-isothiocyanate (RITC), and rhodamine, but not always limited thereto, and any fluorescent material that is well known to those in the art can be used.

In the above method, the micro RNA microarray chip of step 4) is preferably Agilent Human miRNA array v16.0 (Agilent, USA), but not always limited thereto, and any microarray chip loaded with micro RNAs demonstrating upor down-regulation (see Table 1), among human micro RNAs, can be used. The micro RNA microarray chip constructed by the present inventors is more preferred.

In the analyzing method of step 4), GeneSpring GX 11 softwear (Agilent, USA) is preferably used, but not always limited thereto, and any software for such analysis known to those in the art can be used.

The present invention also provides a method for the identification of exposure to lower aliphatic saturated aldehydes comprising the following steps:

1) extracting RNA from somatic cells obtained from both the experimental group and the normal control group;
2) synthesizing cDNA from the RNA obtained from both the experimental group and the control group of step 1);
3) performing real-time RT-PCR (real-time reverse transcript polymerase chain reaction) with the cDNA synthesized from the RNA obtained from both the experimental group and the control group of step 2) using the primer set which is able to amplify the micro RNA integrated on the microarray chip of the present invention; and
4) confirming the expression of the amplified product of step 3) by comparing the expression of the experiment group with that of the control group.

In the above method, the somatic cell of step 1) is preferably human lung cell or human lung cancer cell, but not always limited thereto, and in fact any cell derived from tissue can be used.

In the above method, the human lung cancer cell is preferably A549, but not always limited thereto.

In the above method, the primer of step 3) can be any primer that is able to amplify the biomarker micro RNA screened in this invention.

The present invention also provides a kit for the identification of exposure to lower aliphatic saturated aldehydes comprising the microarray chip of the present invention.

The said kit for the identification of exposure to lower aliphatic saturated aldehydes can additionally include human lung cell or human lung cancer cell, but not always limited thereto.

The human lung cancer cell is preferably A549, but not always limited thereto, and any human lung cell or human lung cancer cell and tissue derived cell can be used.

The kit can additionally include a fluorescent material which is preferably selected from the group consisting of streptavidin-like phosphatase conjugate, chemifluorescence, and chemiluminescent, but not always limited thereto. In a preferred embodiment of the present invention, Cy3 was used.

The kit can additionally include reaction reagent which is exemplified by buffer used for hybridization, labeling reagent such as chemical inducer of fluorescent dye, and washing buffer, but not always limited thereto, and any reaction reagent required for micro RNA microarray chip hybridization known to those in the art can be included.

In addition, the present invention provides a kit for the identification of exposure to lower aliphatic saturated aldehydes comprising the primer set that is complementary to one or more micro RNAs selected from the following group and is able to amplify the said micro RNA:

micro RNA accession number (miRbase) MIMAT0003258 (hsa-miR-590-5p, *Homo sapiens* miR-590-5p; SEQ. ID. NO: 1); and micro RNA accession number (miRbase) MIMAT0000085 (hsa-miR-28-5p, *Homo sapiens* miR-28-5p; SEQ. ID. NO: 2).

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Cytotoxicity of Lower Aliphatic Saturated Aldehydes

<1-1> Cell Culture

A549 cells (Korean Cell Line Bank), the human lung cancer tissue derived cell line, were cultured in 100 mm dish containing RPMI (Gibro-BRL, USA) supplemented with 10% FBS until the confluency reached 80%. The present inventors selected 7 kinds of lower aliphatic saturated aldehydes (propionaldehyde, butylaldehyde, valeraldehyde, hexanal, heptanal, octanal, and nonanal) based on the previous studies and reports and then dissolved in DMSO (dimethyl sulfoxide). The concentration of vehicle was up to 0.1% in every experiment.

<1-2> Cytotoxicity Test (MTT Assay) and Confirmation Of Cytotoxicity by Treating Chemicals MTT assay was performed with A549 cell line according to the method of Mossman, et al (*J. Immunol. Methods*, 65, 55-63, 1983).

Particularly, the cells were distributed in 24-well plate ($3.5 \times 10^5$ cells/well) containing RPMI (Gibro-BRL, USA) and then treated with 7 kinds of lower aliphatic saturated aldehydes (propionaldehyde, butylaldehyde, valeraldehyde, hexanal, heptanal, octanal, and nonanal) selected in Example <1-1> dissolved in DMSO. 48 hours later, 5 mg/ml of MTT (3-4,5-dimethylthiazol-2,5-diphenyltetra zolium bromide) was added thereto, followed by culture at 37° C. for 3 hours. Then, the medium was discarded and the formed formazan crystal was dissolved in 500 µl of DMSO, which was aliquoted in 96-well plate. $OD_{540}$ was measured.

Figure 1:
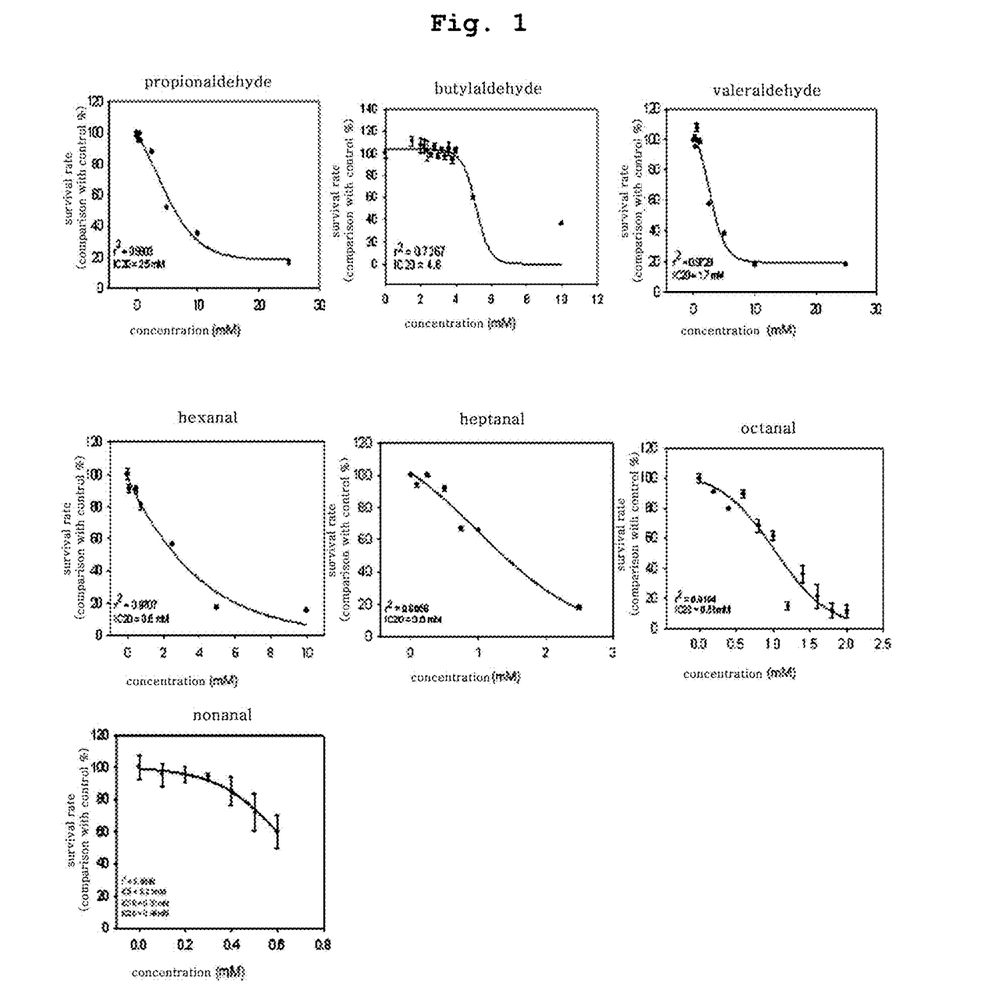
FIG. 1 is a set of graphs illustrating the cytotoxicity of lower aliphatic saturated aldehydes (propionaldehyde, butylaldehyde, valeraldehyde, hexanal, heptanal, octanal, and nonanal) in human lung cancer cell line.

As a result, as shown in FIG. 1, $IC_{20}$ values (the concentration showing 80% cell survival rate) of those lower aliphatic saturated aldehydes were as follows: propionaldehyde, 2.5 mM; butylaldehyde, 4.6 mM; valeraldehyde, 1.7 mM; hexanal, 0.8 mM; heptanal, 0.6 mM; octanal, 0.58 mM; and nonanal, 0.44 mM. Microarray experiment was performed based on the above results (FIG. 1).

Example 2

Expression Pattern of Micro RNA Changed by Lower Aliphatic Saturated Aldehydes, Confirmed by Microarray <2-1> Separation of Target Micro RNA A549 cells were distributed in 6-well plate at the density of $25 \times 10^4$ cells/d, to which lower aliphatic saturated aldehydes (propionaldehyde, butylaldehyde, valeraldehyde, hexanal, heptanal, octanal, and nonanal) were treated for 48 hours at the concentrations determined in Example <1-2>. Then, total RNA was extracted from the cells by using trizol reagent according to the manufacturer's protocol (Invitrogen life technologies, USA). Genomic DNA was eliminated by using RNase-free DNase set (Qiagen, USA) during the RNA purification. The concentration of each total RNA sample was measured by using NanoDrop ND 1000 spectrophotometer (NanoDrop Technologies Inc., USA), and the purity was confirmed by agarose gel electrophoresis.

<2-2> Preparation of Labeled Micro RNA

For oligo microarray analysis, total RNA of the experimental group each treated with different lower aliphatic saturated aldehydes (propionaldehyde, butylaldehyde, valeraldehyde, hexanal, heptanal, octanal, and nonanal) obtained in Example <2-1> was labeled with a fluorescent material.

Particularly, fluorescence labeling was performed according to the manufacturer's protocol by using Agilent miRNA complete labeling and hybridization kit. 0.4 ul of 10× CIP buffer, 1.1 ul of nuclease-free water, and 0.5 ul of Calf Intestinal Phosphatase were added to 2 μl (100 ng) of the obtained total RNA, followed by reaction at 37° C. for 30 minutes. 2.8 ul of 100% DMSO was added to the mixture, followed by reaction for 5~10 minutes and then transferred in ice instantly. For the conjugation with dye, 1 ul of 10× T4 RNA ligase buffer, 3 ul of Cyanine-3-pCp, and 0.5 ul of T4 RNA ligase were added thereto, followed by reaction at 16° C. for 2 hours. The labeled sample was purified by using micro bio-spin 6 column. The purified RNA was completely dried in vacuum concentrator at 55° C., which was then dissolved in 18 ul of nuclease-free water. 4.5 ul of 10× GE blocking agent, and 22.5 ul of 2× Hi-RPM hybridization buffer were added thereto. The prepared sample was reacted at 100° C. for 5 minutes, which was then transferred in ice instantly, followed by reaction for 5 more minutes therein. The sample was used for the hybridization.

<2-3> Hybridization

Hybridization and washing were performed according to the protocol provided by Ebiogen Inc. (Seoul, Korea). Hybridization was performed in a 55° C. oven for 20 hours. Human miRNA array v16.0 (Agilent, USA) was used as the microarray chip.

<2-4> Investigation of Micro RNA Expression Pattern by Using Fluorescence Image

Hybridization images on the slide were scanned with Agilent C scanner (Agilent technologies, USA). The extracted data proceeded to normalization by using Agilent Gene-Spring GX 11 (Agilent technologies) to analyze expression pattern of each gene.

Figure 2:
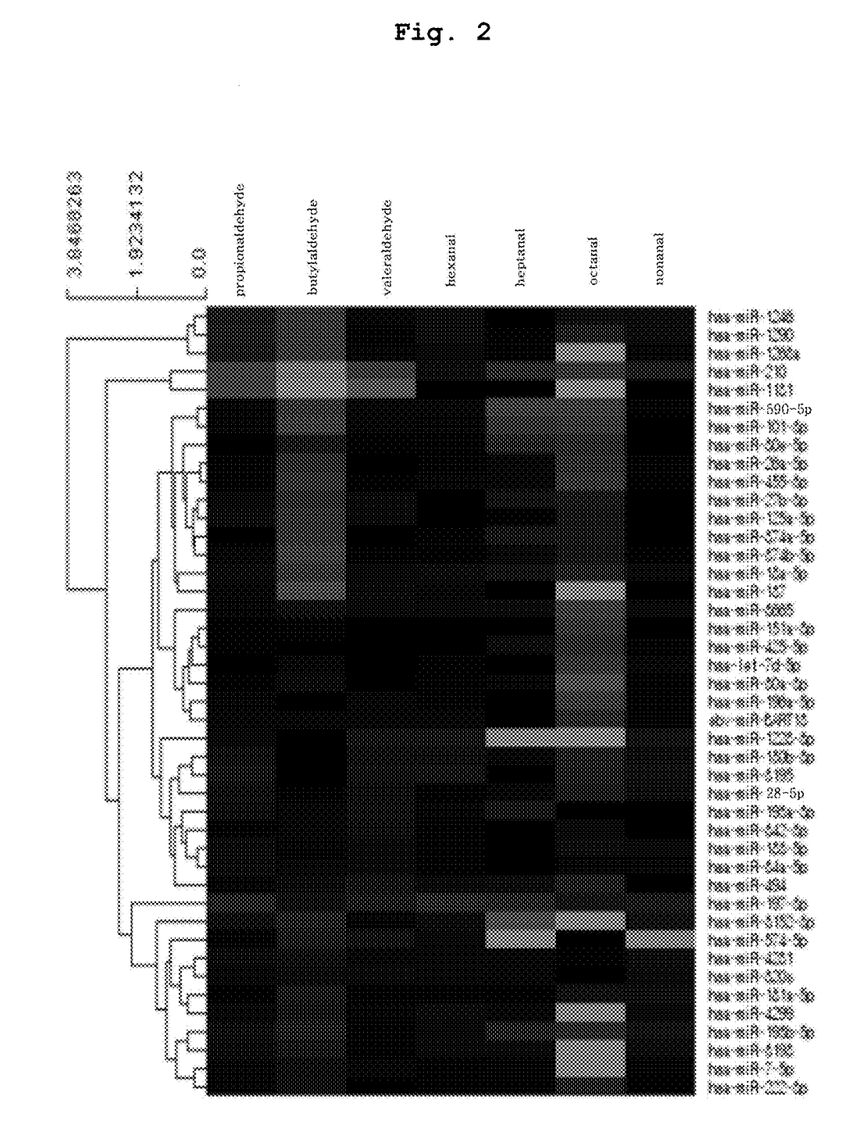
FIG. 2 is a diagram illustrating the result of the analysis on the expression pattern of micro RNA in human lung cancer cell line treated with lower aliphatic saturated aldehydes by using micro RNA microarray chip.

As a result, as shown in FIG. 2 and Table 1, in the sample treated with propionaldehyde at the concentration of $IC_{20}$, the up-regulated micro RNA took 0.97% (13 out of 1347 micro RNAs), and the down-regulated micro RNA took 0.15% (2 out of 1347 micro RNAs). In the sample treated with butylaldehyde, the up-regulated micro RNA took 1.04% (14 out of 1347 micro RNAs), and the down-regulated micro RNA took 0.82% (11 out of 1347 micro RNAs). In the sample treated with valeraldehyde, the over-expressed micro RNAs took 0.59% (8 out of 1347 micro RNAs) and the down-regulated micro RNAs took 0.15% (5 out of 1347 micro RNAs). In the sample treated with hexanal, the up-regulated micro RMA took 0.37% (5 out of 1347 micro RNAs), and the down-regulated micro RNA took 0.07% (1 out of 1347 micro RNAs). In the sample treated with heptanal, the up-regulated micro RNA took 0.00% (0 out of 1347 micro RNAs), and the down-regulated micro RNA took 0.30% (4 out of 1347 micro RNAs). In the sample treated with octanal, the up-regulated micro RNA took 0.07% (one out of 1347 micro RNAs), and the down-regulated micro RNA took 1.04% (14 out of 1347 micro RNAs). In the sample treated with nonanal, the up-regulated micro RNA took 0.45% (6 out of 1347 micro RNAs) and the down-regulated micro RNA took 0.00% (0 out of 1347 micro RNAs). At that time, the micro RNA demonstrating at least 1.5 fold up-regulation by more than 3 kinds of lower aliphatic saturated aldehydes was only one kind, and the micro RNA demonstrating less than 0.66 fold down-regulation by the same was also only one kind (FIG. 2 and Table 1).

TABLE 1

| Accession Number | Gene Name | Change (Fold) | |
|---|---|---|---|
| MIMAT0003258; SEQ. ID. NO: 1 | hsa-miR-590-5p | Propionaldehyde | 1.229 |
| | | Butylaldehyde | 0.563 |
| | | Valeraldehyde | 1.253 |
| | | Hexanal | 1.252 |
| | | heptanal | 0.512 |
| | | Octanal | 0.508 |
| | | nonanal | 0.966 |
| MIMAT0000085; SEQ. ID. NO: 2 | hsa-miR-28-5p | Propionaldehyde | 1.743 |
| | | Butylaldehyde | 0.962 |
| | | Valeraldehyde | 1.660 |
| | | Hexanal | 1.091 |
| | | heptanal | 0.922 |
| | | Octanal | 0.755 |
| | | nonanal | 1.569 |

Example 3

Confirmation of Over-Expression of Micro RNA by Real-Time RT-PCR (Reverse Transcriptase Polymerase Chain Reaction)

The micro RNA over-expressed by the exposure to at least 3 kinds of lower aliphatic saturated aldehydes and the micro RNA down-regulated by the same were selected. These micro RNAs were as follows:

micro RNA accession number (miRbase) MIMAT0003258 (hsa-miR-590-5p, Homo sapiens miR-590-5p; SEQ. ID. NO: 1); and micro RNA accession number (miRbase) MIMAT0000085 (hsa-miR-28-5p, Homo sapiens miR-28-5p; SEQ. ID. NO: 1).

To investigate and quantify the expressions of the said micro RNAs, primers that were capable of expressing specifically the said micro RNAs were constructed (Qiagen, Cat No.: MS00004900(MIMAT0003258), Cat No.: MS00003255(MIMAT0000085). Quantitative real-time RT-PCR was performed with the primers by using My IQ real-time PCR (Bio-rad, USA).

TABLE 2

| Accession Number | Gene Name | sequence of mature micro RNA (5'->3') |
|---|---|---|
| MIMAT0003258 | hsa-miR-590-5p | 5' GAGCUUAUUCAUAAAAGUGCAG (SEQ. ID. NO: 1) |
| MIMAT0000085 | hsa-miR-28-5p | 5' AAGGAGCUCACAGUCUAUUGAG (SEQ. ID. NO: 2) |

<3-1> Construction of cDNA

For oligo microarray analysis, cDNA was first constructed from the total RNA obtained from the groups treated with lower aliphatic saturated aldehydes in Example <2-1>.

Particularly, cDNA was constructed according to the manufacturer's instruction by using miScript RT kit of Qiagen Co. 1 μg of the obtained total RNA was mixed with the reagents as shown in Table 3, followed by reaction at 37° C. for 60 minutes. Another reaction was induced at 95° C. for 5 minutes to inactivate reverse transcriptase.

TABLE 3

| Composition | Volume (µl) |
| --- | --- |
| RT buffer | 4 |
| RNase-free water | variable |
| (Reverse Transcriptase Mix | 1 |
| Template | up to 1µl |
| Total volume | 20 |

<3-2> Confirmation of Changes of Micro RNA Expression by Quantification of PCR Product To quantify PCR product, SYBR green I (Bio-rad, USA) staining was performed. SYBR green I staining is the method taking advantage of intercalating with double-stranded DNA, and thus the more double-stranded DNA is produced, the stronger the fluorescence intensity during PCR. First, as shown in Table 4, target micro RNA was added to universal primer master mix, followed by PCR. Then, primer optimization was performed to determine a proper concentration. The synthesized cDNA was mixed with each primer (Qiagen, Cat No.: MS00004900(MIMAT0003258), Cat No.: MS00003255(MIMAT0000085), to which SYBR green master-mix was added. Then, PCR was performed and the result was analyzed by using quantitative software.

TABLE 4

| Composition | Volume (µl) |
| --- | --- |
| SYBR Green Master Mix | 5 |
| Universal Primer | 1 |
| Primer | 1 |
| RNase-free water | 3.8 |
| Template cDNA | 0.2 |

Figure 3:
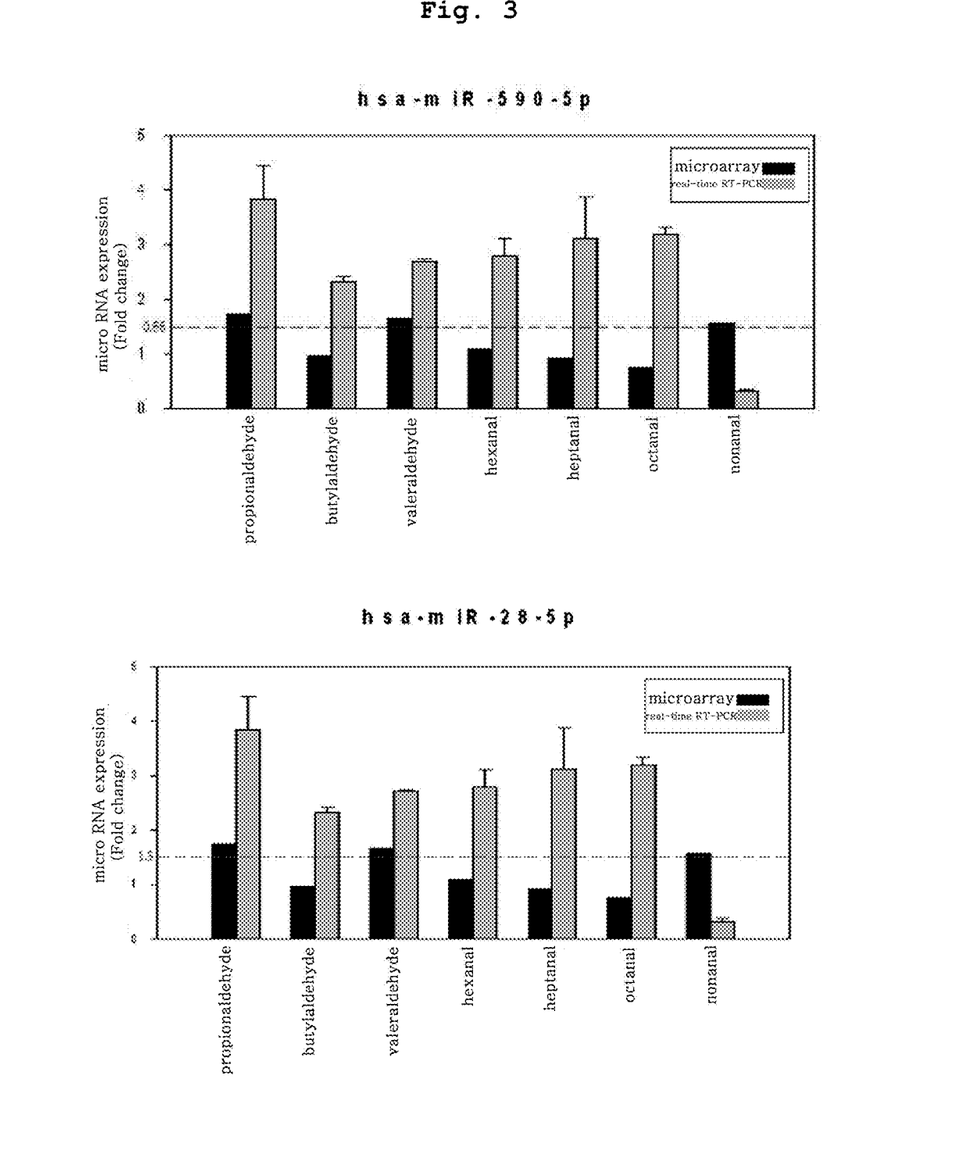
FIG. 3 is a set of graphs illustrating the comparison of expression patterns of 2 kinds of micro RNAs showing expressional changes by lower aliphatic saturated aldehydes obtained by using oligomicroarray chip and real-time RT-PCR (reverse transcript polymerase chain reaction).

As a result, as shown in FIG. 3, one micro RNA up-regulated and one micro RNA down-regulated were confirmed, which was consistent with the result obtained above from oligo microarray investigating micro RNA expression pattern by the treatment of lower aliphatic saturated aldehydes (FIG. 3).

INDUSTRIAL APPLICABILITY

As explained hereinbefore, the present invention can be effectively used for the monitoring of lower aliphatic saturated aldehydes having toxicity to cause diverse diseases in human and for the risk assessment thereof and also as a tool to investigate toxicity mechanism caused by lower aliphatic saturated aldehydes.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for the identification of exposure to a lower aliphatic saturated aldehyde selected from the group consisting of butyraldehyde, heptanal, octanal, propionaldehyde, valeraldehyde and nonanal, comprising the following steps:
   1) measuring an expression level of a micro RNA (ribonucleic acid) hsa-miR-590-5p with a nucleotide sequence of SEQ. ID. NO: 1, and a micro RNA hsa-miR-28-5p with a nucleotide sequence of SEQ. ID. NO: 2 in somatic cells isolated from an experimental group and a normal control group, respectively; and
   2) determining the experimental group to be exposed to:
      a) butyraldehyde, heptanal or octanal when the expression level of micro RNA accession number hsa-miR-590-5p is down-regulated in the somatic cells isolated from the experimental group in comparison with the somatic cells from the normal control group; and
      b) propionaldehyde, valeraldehyde or nonanal when the expression level of micro RNA accession number hsa-miR-28-5p is up-regulated in the somatic cells isolated from experimental group comparison with the somatic cells isolated from the normal control group.

2. The method for the identification of exposure to a lower aliphatic saturated aldehyde according to claim 1, wherein the somatic cells of step 1) are human lung cells or human lung cancer tissue derived cells.

3. A method for the identification of exposure to a lower aliphatic saturated aldehyde selected from the group consisting of butyraldehyde, heptanal, octanal, propionaldehyde, valeraldehyde and nonanal, comprising the following steps:
   1) extracting RNA from somatic cells obtained from an experimental group and a normal control group, respectively;
   2) labeling the RNA obtained from the experimental group of step 1) with a first fluorescent material and the RNA from the control group of step 1) with a second fluorescent material;
   3) hybridizing the RNA labeled with the first and second fluorescent materials of step 2) with a microarray chip on which one or more micro RNAs selected from the following group or complementary strand molecules thereof are integrated:
      micro RNA hsa-miR-590-5p, with a nucleotide sequence of SEQ. ID. NO: 1; and
      micro RNA hsa-miR-28-5p, with a nucleotide sequence of SEQ. ID. NO: 2);
   4) analyzing the microarray chip reacted in step 3); and
   5) determining the experimental group to be exposed to:
      a) a lower aliphatic saturated aldehyde selected from the group consisting of butyraldehyde, heptanal, and octanal, when the data analysis of step 4) indicates that the expression level of micro RNA hsa-miR-590-5p is down-regulated in comparison with the normal control group, and
      b) a lower aliphatic saturated aldehyde selected from the group consisting of propionaldehyde, valeraldehyde and nonanal, when the data analysis of step 4) indicates that the expression level of micro RNA hsa-miR-28-5p is up-regulated in comparison with the normal control group.

4. The method for the identification of exposure to a lower aliphatic saturated aldehyde according to claim 3, wherein the somatic cell of step 1) is human lung cell or human lung cancer cell.

5. The method for the identification of exposure to a lower aliphatic saturated aldehyde according to claim 4, wherein the human lung cancer cell is A549.

6. The method for the identification of exposure to a lower aliphatic saturated aldehyde according to claim 3, wherein the fluorescent materials of step 2) are each selected from the group consisting of Cy3 (Cyanine 3), Cy5 (Cyanine 5), poly L-lysine-fluorescein isothiocyanate (FITC), rhodamine-B-isothiocyanate (RITC), and rhodamine.

7. A method for the identification of exposure to a lower aliphatic saturated aldehyde selected from the group consisting of butyraldehyde, heptanal, octanal, propionaldehyde, valeraldehyde and nonanal, comprising the following steps:
   1) extracting RNA from somatic cells obtained from an experimental group and a normal control group;
   2) synthesizing cDNA from the RNA obtained from the experimental group and the control group of step 1);
   3) performing real-time RT-PCR (real-time reverse transcript polymerase chain reaction) with the cDNA synthesized from the RNA obtained from the experimental group and the control group of step 2) using a primer set which is able to amplify the micro RNA hsa-miR-590-5p, with a nucleotide sequence of SEQ. ID. NO: 1 or micro RNA hsa-miR-28-5p, with a nucleotide sequence of SEQ. ID. NO: 2, respectively; and
   4) determining the experimental group to be exposed to:
      a) butyraldehyde, heptanal or octanal when the expression level of the amplified product of the RNA obtained from the experimental group generated by the RT-PCR using the primer set which is able to amplify the micro RNA hsa-miR-590-5p is down-regulated in comparison with the amplified product of the RNA obtained from the normal control group, and
      b) propionaldehyde, valeraldehyde or nonanal when the expression level of the amplified product of the RNA obtained from the experimental group generated by the RT-PCR using the primer set which is able to amplify the micro RNA hsa-miR-28-5p is up-regulated in comparison with the amplified product of the RNA obtained from the normal control group.

8. The method for the identification of exposure to a lower aliphatic saturated aldehyde according to claim 7, wherein the somatic cell of step 1) is a human lung cell or human lung cancer cell.

9. The method for the identification of exposure to a lower aliphatic saturated aldehyde according to claim 8, wherein the human lung cancer cell is A549.

* * * * *